US012330128B2

(12) United States Patent
Winkelmann et al.

(10) Patent No.: US 12,330,128 B2
(45) Date of Patent: Jun. 17, 2025

(54) PROCESS FOR PREPARING AN AQUEOUS DISPERSION OF MICROPARTICLES

(71) Applicant: BASF SE, Ludwigshafen am Rhein (DE)

(72) Inventors: Marion Winkelmann, Ludwigshafen (DE); Kerstin Muelheims, Ludwigshafen (DE); Ralph Tauber, Gerolsheim (DE); Yannick Fuchs, Speyer (DE); Murat Cetinkaya, XZ Den Haag (NL); Bernd Sachweh, Meckenheim (DE)

(73) Assignee: BASF SE, Ludwigshafen am Rhein (DE)

( * ) Notice: Subject to any disclaimer, the term of this patent is extended or adjusted under 35 U.S.C. 154(b) by 182 days.

(21) Appl. No.: 15/769,158

(22) PCT Filed: Oct. 20, 2016

(86) PCT No.: PCT/EP2016/075187
§ 371 (c)(1),
(2) Date: Apr. 18, 2018

(87) PCT Pub. No.: WO2017/068024
PCT Pub. Date: Apr. 27, 2017

(65) Prior Publication Data
US 2018/0297001 A1    Oct. 18, 2018
US 2020/0139331 A9    May 7, 2020

(30) Foreign Application Priority Data

Oct. 22, 2015 (EP) .................................. 15191091

(51) Int. Cl.
| | |
|---|---|
| *B01J 13/02* | (2006.01) |
| *A01N 25/04* | (2006.01) |
| *A01N 25/28* | (2006.01) |
| *A61K 9/14* | (2006.01) |
| *A61K 9/50* | (2006.01) |
| *B01J 13/18* | (2006.01) |
| *C09B 67/02* | (2006.01) |
| *A01N 43/54* | (2006.01) |

(52) U.S. Cl.
CPC .............. *B01J 13/18* (2013.01); *A01N 25/04* (2013.01); *A01N 25/28* (2013.01); *A61K 9/145* (2013.01); *A61K 9/5089* (2013.01); *C09B 67/0097* (2013.01); *A01N 43/54* (2013.01); *A01N 2300/00* (2013.01)

(58) Field of Classification Search
CPC ........ A61K 9/50; A61K 9/501; A61K 9/5015; A61K 9/5021; A61K 9/5089; B01J 13/02
See application file for complete search history.

(56) References Cited

U.S. PATENT DOCUMENTS

| | | | |
|---|---|---|---|
| 4,406,816 A | | 9/1983 | Sliwka |
| 4,557,755 A | * | 12/1985 | Takahashi ................ B01J 13/18 514/936 |
| 4,898,696 A | | 2/1990 | Sliwka |
| 4,918,317 A | | 4/1990 | Hess et al. |
| 4,957,666 A | * | 9/1990 | Kawamura .............. B01J 13/18 264/4.3 |
| 5,162,486 A | | 11/1992 | Follmann et al. |
| 5,462,915 A | | 10/1995 | Curtis et al. |
| 6,214,331 B1 | * | 4/2001 | Vanderhoff ............. A61L 27/16 424/423 |
| 6,224,795 B1 | | 5/2001 | Frank et al. |
| 6,261,483 B1 | | 7/2001 | Frank et al. |
| 2002/0115569 A1 | * | 8/2002 | Schnabel ............... A01N 37/40 504/310 |
| 2007/0248824 A1 | * | 10/2007 | Lang-Wittkowski ...... B01J 2/20 428/402.24 |

(Continued)

FOREIGN PATENT DOCUMENTS

| | | |
|---|---|---|
| DE | 19833347 A1 | 1/2000 |
| DE | 19835114 A1 | 2/2000 |
| EP | 0026914 A1 | 4/1981 |

(Continued)

OTHER PUBLICATIONS

Bone et al, Microencapsulated Fragrances in Melamine Formaldehyde Resins, 2011, Popular Scientific Papers, vol. 65, No. 3 (Year: 2011).*
Bone et al (Bone et al (Microencapsulated Fragrances in Melamine Formaldehyde Resins; International Year of Chemistry 2011, 65, No. 3 hereafter Bone) (Year: 2011).*
Bone et al (Microencapsulated Fragrances in Melamine Formaldehyde Resins; International Year of Chemistry 2011, 65, No. 3 (Year: 2011).*

(Continued)

*Primary Examiner* — Micah Paul Young
(74) *Attorney, Agent, or Firm* — Armstrong Teasdale LLP

(57) ABSTRACT

Provided herein is a process for preparing an aqueous dispersion of microparticles containing a water-insoluble, solid, non-polymeric, organic active or functional material (M) and an aminoplast resin (A) which surrounds or embeds material (M). The process includes the following steps: i) providing an aqueous slurry of the material (M) in the form of coarse particles; ii) subjecting the aqueous slurry to shear forces such that the coarse particles of the material (M) are comminuted and an aqueous suspension of fine particles of the material (M) is obtained; and iii) performing a polycondensation of an aminoplast pre-condensate during step (ii) or in the aqueous suspension of the fine particles of the material (M) obtained in step (ii); wherein step (ii) is performed in the presence of at least one protective colloid and in the presence of at least a portion of the aminoplast pre-condensate subjected to the polycondensation of step (iii).

15 Claims, No Drawings

(56) References Cited

U.S. PATENT DOCUMENTS

| | | | |
|---|---|---|---|
| 2013/0287844 A1 | 10/2013 | Taranta et al. | |
| 2016/0088837 A1* | 3/2016 | Uhr | A01N 25/28 504/159 |

FOREIGN PATENT DOCUMENTS

| | | | | |
|---|---|---|---|---|
| EP | 0218887 | A2 | 4/1987 | |
| EP | 0319337 | A1 | 6/1989 | |
| EP | 0383337 | A2 | 8/1990 | |
| EP | 0415273 | A2 | 3/1991 | |
| EP | 2801256 | A1 * | 11/2014 | A01N 25/28 |
| SU | 452938 | A3 | 12/1974 | |
| SU | 692543 | A3 | 10/1979 | |
| SU | 967269 | A3 | 10/1982 | |
| WO | 9513698 | A1 | 5/1995 | |
| WO | 9603041 | A1 | 2/1996 | |
| WO | 9633611 | A2 | 10/1996 | |
| WO | 0027519 | A2 | 5/2000 | |
| WO | 0151197 | A1 | 7/2001 | |
| WO | 2007072046 | A2 | 6/2007 | |
| WO | 2008043835 | A2 | 4/2008 | |
| WO | 2008043836 | A1 | 4/2008 | |
| WO | 2008155097 | A2 | 12/2008 | |
| WO | 2009098232 | A1 | 8/2009 | |
| WO | 2011064312 | A1 | 6/2011 | |
| WO | WO-2012095436 | A1 * | 7/2012 | A01N 25/28 |
| WO | WO-2015031418 | A1 * | 3/2015 | A61K 8/11 |
| WO | PCT-2017/021159 | A1 | 2/2017 | |

OTHER PUBLICATIONS

International Search Report and Written Opinion for International Application No. PCT/EP2016/075187, Dec. 21, 2016, 11 pages.
European Search Report for EP Patent Application No. 15191091.6, Issued on May 10, 2016, 5 pages.

\* cited by examiner

PROCESS FOR PREPARING AN AQUEOUS DISPERSION OF MICROPARTICLES

CROSS-REFERENCE TO RELATED APPLICATIONS

This application is the national stage entry of PCT/EP2016/075187, filed on Oct. 20, 2016, which claims the benefit of priority to European Patent Application No. 15191091.6, filed Oct. 22, 2015, which are incorporated by reference in their entirety herein.

The present invention relates to a process for preparing an aqueous dispersion of microparticles containing a solid non-polymeric, organic agriculturally active material M and an aminoplast resin A which surrounds or embeds material M.

BACKGROUND

Microparticles containing non-polymeric organic active materials, such as pesticides and pharmaceuticals, embedded or surrounded by a polymer material have often been described in the literature. The reasons for embedding or surrounding the active material in a polymer material, also termed microencapsulation, are manifold and include, e.g.
  enabling safe and practical handling of toxic or perishable substances;
  achieve steady, controlled release of material;
  prevent mixing of substances;
  modify surface properties,
  improving formulation stability, reduction of agglomeration or crystallization.

Microencapsulation of active organic material can be principally achieved by coacervation techniques, spray drying, fluidized-bed coating, electrostatic microencapsulation or in-situ polymerization. These techniques provide particles of the active or functional organic material, wherein the active compound is surrounded or embedded by a polymeric wall material.

The most common method for microencapsulation of pesticides is the interfacial polymerization. In this process, a first reactant, e.g. a polyfunctional isocyanate or acid chloride, is dissolved in the liquid pesticide ingredient or a solution thereof, which is then dispersed in water and subjected to polymerization by addition of a polyfunctional compound having a complementary reactivity with regard to the first reactant, e.g. an diamine or diol. The polymerization occurring at the interface between the active substance and the aqueous phase completely encloses the fine droplets of pesticide substance with a thin membrane of polyurea or polyamide.

Modern techniques of microencapsulation active or functional organic material include the radical suspension polymerization of water-insoluble acrylate monomers with (meth)acrylic acid and optionally polyfunctional monomers in the presence of an o/w-emulsion of the active or functional organic material or the radical emulsion polymerization of an aqueous monomer emulsions, wherein the active or functional organic material is dissolved or suspended in the monomer droplets.

A further in-situ polymerization technique includes microencapsulation of liquids by using aminoplasts, such as melamine formaldehyde resins (MF resins) or urea formaldehyde resins (UF resins) or melamine formaldehyde urea resins (MUF resins). The aminoplast resins are used in the form of their prepolymers or pre-condensates, which are added to an aqueous emulsion of the material to be encapsulated and cured by heating and/or altering the pH of the reaction mixture to effect polymerization of the prepolymers. Thereby, an aqueous suspension of the microcapsules are obtained, where the particles of the encapsulated material are surrounded by or embedded in an aminoplast polymer.

Microencapsulation of pesticides using in-situ polymerization of aminoplasts pre-condensates have been described several times. For example, U.S. Pat. No. 4,557,755 describes the microencapsulation of water-insoluble pesticides by polymerizing an aminoplast pre-condensate, such as a melamine formaldehyde or melamine urea formaldehyde resin in an aqueous suspension of the pesticide compound in the presence of a cationic urea resin. The method is suggested for certain insecticides and fungicides.

U.S. Pat. No. 5,462,915 describes an improved process for microencapsulation of water-insoluble pesticides, which comprises adding to a suspension of the pesticide a liquid aminoplast prepolymer and curing the prepolymer at temperatures of above 100° C. The method was applied for microencapsulation of water-insoluble salts of dicamba. A similar process is known from WO 00/27519, which was applied for microencapsulation of carbofuran.

WO 96/03041 describes a microcapsule composition of pesticides, wherein the microcapsules have an outer aminoplast layer and an inner wax coating deposited around pesticide compound.

Although microencapsulation of active organic compounds may be beneficial, it is often difficult to achieve, in particular in case of solid organic materials. When trying to microencapsulate a solid organic material in an aqueous suspension of the solid organic material by an in-situ-polymerization technique, the solid organic material tends to agglomerate thereby forming large particles of the organic material, which are embedded in the polymer matrix. A thus obtained suspension is usually no longer suitable for most uses.

The preparation of microparticles of water-insoluble, solid, active organic material usually requires providing an aqueous suspension of fine particles of the water-insoluble, solid organic material to be encapsulated, because most of the microencapsulating techniques are performed in an aqueous reaction medium. For this, the solid organic material must usually be comminuted before it is microencapsulated, as the water-insoluble, solid organic material is normally present as coarse solid particles, such as crystals, having particles sizes of 100 µm or higher, which are unsuitable for microencapsulation. Although one may comminute the coarse solid material in the dry state to a powder, this procedure is tedious and unsatisfactory, as the powder must be dispersed in water prior to microencapsulation and, hence, preparation of a powder requires an additional process step. Apart from that, organic powders are difficult to handle as they tend to agglomerate and bear an explosion risk.

Although it is desirable to comminute the water-insoluble, solid active organic material to be encapsulated directly in an aqueous suspension of the material, one often encounters the problem that the suspension becomes highly viscous upon comminution and/or forms foam due to inclusion of air. This becomes particularly problematic for water-insoluble organic compounds bearing aromatic and other non-polar functional groups, as found in e.g. in pesticides or pharmaceuticals, because these non-polar moieties tend to reduce surface tension of water and stabilize gas bubbles in the aqueous continuous phase. Moreover, surfactants which are used to stabilize the fine particles in the suspension also favor foam formation. So far, large amounts of antifoam agents are required, in order to allow for efficiently comminuting such solid organic materials in an aqueous suspension. However, the presence of anti foaming agents in the final product is not always favorable and might interfere with the encapsulation procedure.

SUMMARY OF INVENTION

It is an object to provide a process for microencapsulating solid, water-insoluble non-polymeric organic active materials, such as pesticides or pharmaceuticals, without the need for providing a powder of the materials prior to encapsulation. In particular, the process should be suitable for preparing aqueous suspensions of microparticles, especially of microparticles, which contain solid organic pesticide compounds, which usually are difficult to comminute in aqueous media without any anti foaming agents due to the presence of polar functional moieties.

It was surprisingly found that solid, water-insoluble non-polymeric organic active materials, in particular solid organic pesticide compounds, can be efficiently microencapsulated, if the comminution of the coarse solid, water-insoluble non-polymeric organic active or functional materials to be encapsulated is performed in the presence of an aminoplast pre-condensate used for the microencapsulation of the solid, water-insoluble non-polymeric organic active materials and a protective colloid. Polycondensation of the aminoplast pre-condensate in the thus obtained aqueous suspension of the fine particles of said material yields an aqueous dispersion of microparticles containing the water-insoluble, solid, non-polymeric, organic active material and an aminoplast resin A which surrounds or embeds the organic material.

Therefore, the present invention relates to a process for preparing an aqueous dispersion of microparticles containing a water-insoluble, solid, non-polymeric, organic active material M, which is selected from the group consisting of agriculturally active compounds, and an aminoplast resin A which surrounds or embeds the material M, which comprises the following steps:
i. providing an aqueous slurry of the material M in the form of coarse particles
ii. subjecting the aqueous slurry to shear forces, e.g. by milling or grinding, such that the coarse particles of the material M are comminuted and an aqueous suspension of fine particles of the material M is obtained;
iii. performing a polycondensation of an aminoplast pre-condensate during step ii. or in the aqueous suspension of the fine particles of the material M obtained in step ii.;
wherein step ii. is performed in the presence of at least one protective colloid and in the presence of at least a portion of the aminoplast pre-condensate subjected to the polycondensation of step iii.

The process of the invention allows for efficiently comminuting the coarse particles of the material M without significant formation of foam, even at high loadings of the slurry with the material M. Without being bound to theory, it is believed that the aminoplast pre-condensate acts as a defoamer, thereby reducing formation of foam and viscosity during the comminution process. Thereby conventional defoamers, which are normally required during comminution can be avoided or their amount can be reduced significantly.

DETAILED DESCRIPTION OF INVENTION

The expression "wt %" as used herein means "% by weight".

Here and throughout the specification, the terms "microparticles" and "microcapsules" are used synonymously and relate to particles which contain the agriculturally active compound and an aminoplast resin which surrounds or embeds the solid agriculturally active compound. The terms "microparticles" and "microcapsules" indicates that the discrete particles having usually a particle size of less than 200 μm in particular less than 100 μm, given as d(0.9) value.

In the first step of the method of the present invention, an aqueous slurry of coarse particles of the material M is provided. The term "coarse particle" means that the particles of the material M are bigger than the particles usually contained in a suspension concentrate formulation, which means that the volume average diameter d(0.5) of the particles of the material M generally exceeds 20 μm, and is in particular at least 30 μm or at least 50 μm and may range from 20 μm to 2000 μm, in particular in the range of 30 μm to 1000 μm or in the range of 50 μm to 500 μm. Moreover, the d(0.1) value of particles in the slurry is frequently at least 10 μm, i.e. the at most 10 volume % of the particles of the material M in the slurry have a diameter of above 10 μm.

The average particle diameter, as referred herein, is the volume average particle diameter d(0.5) or d(v, 0.5), respectively, i.e. 50 vol.-% of the particles have a diameter which is above the value cited and 50 vol.-% of the particles have a diameter which is below the value cited. Therefore, average particle diameters are also termed "volume median diameters". Such average particle diameters can be determined by dynamic light scattering (usually performed on diluted suspensions containing from 0.01 to 5% by weight of the material M). The d(0.9) or d(v, 0.9) value of particles indicates that 90 vol.-% of the particles are smaller than the value cited. The d(0.1) or d(v, 0.1) value of particles indicates that 10 vol.-% of the particles are smaller than the value cited.

The material M can be principally any active organic compound, such as a pesticide or pharmaceutical compound, which is non-polymeric, i.e. which has a defined molecular structure, which is solid and which is essentially insoluble in water.

Solid means that the melting point of the material M is higher than ambient temperature. In particular the melting point of the material M is at least 50° C., in particular at least 60° C. or at least 70° C. and especially at least 80° C., e.g. from 50 to 300° C. or from 60 to 300° C. or from 70 to 300° C. or from 80 to 300° C.

Essentially water insoluble means that the solubility of the material M in deionized water is at most 5 g/L at 22° C. and 1 bar.

In particular, the material M bears at least one polar moiety, e.g. a heterocylic moiety, in particular a heterocyclic moiety bearing one or more nitrogen atoms as ring memberes and/or one or more polar functional groups. Examples of heterocycles include in particular 5- or 6-membered, monocyclic hetaryl groups such as pyrazolyl, imidazolyl, triazolyl, pyridyl, pyrimidinyl, pyridazinyl, pyrazinyl, triazinyl, 8 to 10 membered fused bicyclic hetaryl such as indolyl, isoindolyl, indazolyl, benzimidazolyl, benzothiazolyl, benzoxazolyl, quinolinyl, isoquinolinyl, phthalazinyl, pyrazolopyridinyl, pyrazolopyrimidinyl, imidazolylpyridinyl or imidazolylpyrimidinyl and the keto-analogues thereof such as imidazolin-2-onyl, pyrazol-3-onyl, pyridine-2-onyl, pyrimidine-2-onyl, pyrimidine-4-onyl, pyrimidine-2,4-dionyl, pyridazin-3-onyl, isoindolin-5-only, quinolin-2-onyl, isoquinolin-1-onyl, phthalazin-3-only etc. Examples of polar functional groups include are not limited to hydroxyl, amino, carbonyl group, including amide and carboxyl groups but also aldehyde or keto groups, imino groups, oxime groups etc.

According to the present invention the material M is an agriculturally active compound.

The term "agriculturally active compound" usually refers to any organic compound which is active against certain agriculturally relevant pests, such as plant pathogenous fungi, undesired vegetation or invertebrate pests such as insects, arachnids, slugs or worms. The term "pesticide compound" thus refers in particular to herbicide compounds, fungicide compounds, insecticide compounds, compounds having acaricidal activity, i.e. acaricides, molluscicides and nematicides in particular to at least one organic active compound selected from the group of the fungicides, insecticides, nematicides, herbicides and biopesticides. Preferred pesticide compounds are fungicides, insecticides and herbicides. Especially preferred pesticide compounds are herbicides. Mixtures of pesticides of two or more of the abovementioned classes may also be used. The skilled worker is familiar with such pesticides, which can be found, for example, in the Pesticide Manual, 17th Ed. (2015), The British Crop Protection Council, London. Suitable insecticides include e.g. insecticides from the class of the carbamates, organophosphates, organochlorine insecticides, phenylpyrazoles, pyrethroids, neonicotinoids, spinosins, avermectins, milbemycins, juvenile hormone analogs, alkyl halides, organotin compounds nereistoxin analogs, benzoylureas, diacylhydrazines, METI acarizides, and insecticides such as chloropicrin, pymetrozin, flonicamid, clofentezin, hexythiazox, etoxazole, diafenthiuron, propargite, tetradifon, chlorfenapyr, DNOC, buprofezine, cyromazine, amitraz, hydramethylnon, acequinocyl, fluacrypyrim, rotenone, or their derivatives. Suitable fungicides include e.g. fungicides from the classes of dinitroanilines, allylamines, anilinopyrimidines, antibiotics, aromatic hydrocarbons, benzenesulfonamides, benzimidazoles, benzisothiazoles, benzophenones, benzothiadiazoles, benzotriazines, benzyl carbamates, carbamates, carboxamides, carboxylic acid diamides, chloronitriles cyanoacetamide oximes, cyanoimidazoles, cyclopropanecarboxamides, dicarboximides, dihydrodioxazines, dinitrophenyl crotonates, dithiocarbamates, dithiolanes, ethylphosphonates, ethylaminothiazolecarboxamides, guanidines, hydroxy-(2-amino)pyrimidines, hydroxyanilides, imidazoles, imidazolinones, inorganic substances, isobenzofuranones, methoxyacrylates, methoxycarbamates, morpholines, N-phenylcarbamates, oxazolidinediones, oximinoacetates, oximinoacetamides, peptidylpyrimidine nucleosides, phenylacetamides, phenylamides, phenylpyrroles, phenylureas, phosphonates, phosphorothiolates, phthalamic acids, phthalimides, piperazines, piperidines, propionamides, pyridazinones, pyridines, pyridinylmethylbenzamides, pyrimidinamines, pyrimidines, pyrimidinonehydrazones, pyrroloquinolinones, quinazolinones, quinolines, quinones, sulfamides, sulfamoyltriazoles, thiazolecarboxamides, thiocarbamates, thiophanates, thiophenecarboxamides, toluamides, triphenyltin compounds, triazines, triazoles. Suitable herbicides include e.g. herbicides from the classes of the acetamides, amides, aryloxyphenoxypropionates, benzamides, benzofuran, benzoic acids, benzothiadiazinones, bipyridylium, carbamates, chloroacetamides, chlorocarboxylic acids, cyclohexanediones, dinitroanilines, dinitrophenol, diphenyl ether, glycines, imidazolinones, isoxazoles, isoxazolidinones, nitriles, N-phenylphthalimides, oxadiazoles, oxazolidinediones, oxyacetamides, phenoxycarboxylic acids, phenylcarbamates, phenylpyrazoles, phenylpyrazolines, phenylpyridazines, phosphinic acids, phosphoroamidates, phosphorodithioates, phthalamates, pyrazoles, pyridazinones, pyridines, pyridinecarboxylic acids, pyridinecarboxamides, pyrimidinediones, pyrimidinyl(thio)benzoates, quinolinecarboxylic acids, semicarbazones, sulfonylaminocarbonyltriazolinones, sulfonylureas, tetrazolinones, thiadiazoles, thiocarbamates, triazines, triazinones, triazoles, triazolinones, triazolocarboxamides, triazolopyrimidines, triketones, uracils and ureas.

The term "agriculturally active compound" also includes pesticide safener compounds. The term "pesticide safener compound" principally includes any organic compound which is provides plants from phytotoxic damage exerted by certain agriculturally relevant pesticide compounds.

The term "agriculturally active compound" also includes plant growth regulators.

Suitable pesticides include in particular the following compounds: herbicides, such as saflufenacil, pyroxasulfon, water-insoluble salts of dicamba, diuron, trifludimoxazin and pendimethalin; fungicides, such as pyrimethanil, pyraclostrobin and fluxapyroxad; insecticides, such as alpha cypermethrin and afidopyropen. The pesticide names are so called common names according to ISO 1750 and include the compounds as such, their salts and their derivatives, provided they are solid and essentially insoluble in water.

The material M may be crystalline or amorphous and is in particular at least partly or completely crystalline. In particular, the degree of crystallinity is at least 90%.

A particular embodiment to the invention relates to microcapsules, wherein the material is saflufenacil, i.e. N'-{2-Chloro-4-fluoro-[1,2,3,6-tetrahydro-3-methyl-2,6-dioxo-4-(trifluoromethyl)pyrimidin-1-yl]benzoyl}-N-isopropyl-N-methylsulfamide. The saflufenacil used in the process of the invention may be any known form of solid saflufenacil, including amorphous saflufenacil and in particular crystalline saflufenacil, e.g. the crystalline anhydrate of saflufenacil as described in WO 08/043835 or a crystalline hydrate of saflufenacil as described in WO 08/043836.

Another particular embodiment to the invention relates to microcapsules, wherein the material M is pyrimethanil, i.e. 4,6-dimethyl-N-phenylpyrimidin-2-amine.

The slurry of the material M can be simply provided by suspending material M in water, which may or may not contain at least a portion of the protective colloid and/or at least a portion of the aminoplast precondensate used for encapsulation. Usually, the amount of solid material M is suspended such that the concentration of the material M in the slurry prior to step ii. is in the range of 5 to 40% by weight, in particular in the range of 7 to 35% of the total weight of the slurry.

According to the invention, step ii. is performed in the presence of the aminoplast pre-condensate used for encapsulation of the material M. During step ii. at least a portion or the total amount of aminoplast pre-condensate subjected to the polycondensation of step iii. may be present. It is also possible that a portion of the aminoplast pre-condensate subjected to the polycondensation of step iii. is added after step ii. has been performed. Usually, at least 20%, in particular at last 50%, especially at least 70% or at least 90% or the total amount of the aminoplast pre-condensate subjected to the polycondensation of step iii. will already be present during step ii.

The aminoplast pre-condensate present during step ii. may be added to the aqueous slurry of the material M provided in step i. or it may be added during step ii. Frequently, the major amount of aminoplast pre-condensate present during step ii. is added to the slurry before starting the comminution of step ii. In particular at least 20%, in particular at least 50%, especially at least 70% or at least 90% of the total amount of aminoplast pre-condensate subjected to the polycondensation of step iii. is added to the slurry of the material M before starting the comminution of step ii.

The concentration of the aminoplast pre-condensate in the slurry of step i. or during comminution of step ii. is frequently in the range of 0.5 to 20% by weight, in particular in the range of 1 to 10% by weight. Preferably, the aminoplast pre-condensate is present in the aqueous slurry of step i. or in the suspension of step ii. in an amount in the range of 1 to 50% by weight, in particular in the range of 1 to 30% by weight and especially in the range of 5 to 25% by weight, based on the material M.

Suitable aminoplast pre-condensates are oligomeric or polymeric condensation products of one or more aldehydes, such as formaldehyde, acetaldehyde, propanal, glyoxal or glutaraldehyde, with one or more amino compounds having usually at least two primary amino groups, such as urea, thiourea, melamine, which may be wholly or partially etherified, cyanoguanamine (=dicyandiamide) and benzoguanamine. Upon applying curing conditions they form cross-linked aminoplast polymers. Aminoplast pre-condensates include, but are not limited to condensation products of melamine and formaldehyde (melamine-formaldehyde pre-condensates or MF pre-condensates), including wholly or partially etherified melamine-formaldehyde condensates, urea-formaldehyde pre-condensates (UF pre-condensates), thiourea-formaldehyde pre-condensates (TUF pre-condensates), pre-condensates of melamine, urea and formaldehyde (MUF pre-condensates), including wholly or partially etherified melamine-urea-formaldehyde condensates, pre-condensates of melamine, thiourea and formaldehyde (MTUF pre-condensates), including partially etherified melamine-thiourea-formaldehyde condensates, urea-glutaraldehyde pre-condensates, benzoguanamine-formaldehyde pre-condensates, dicyandiamide formaldehyde pre-condensates and urea-glyoxal pre-condensates.

Suitable aminoplast pre-condensates for microencapsulation are known and can be found, inter alia, in Kirk-Othmer, Encyclopedia of Chemical Technology, 3rd edition, Vol. 2, pp. 440-469, the prior art cited in the introductory part, U.S. Pat. No. 4,918,317, EP 26914, EP 218887, EP 319337, EP 383,337, EP 415273, DE 19833347, DE 19835114 and WO 01/51197. Suitable pre-condensates are commercially available, e. g. Cymel types, such as but not limited to Cymel® 303, 327, 328 or 385 (etherified melamine formaldehyde resins of Cytec), Maprenal® types, such as but not limited to Maprenal® MF 900w/95, MF 915/751B, MF 920/75WA, MF 921w/85WA, (etherified melamine formaldehyde resins of Ineos), Kauramin® types of BASF SE, such as but not limited to Kauramin® 783, Kauramin® 792 or Kauramin® 753 (melamine formaldehyde resins), Kauramin® 620 or Kauramin® 621 (melamine urea formaldehyde resins), Kaurit® types of BASF SE, such as but not limited to Kaurit® 210, 216, 217 or 220 (urea formaldehyde resins), Luracoll® types such as Luracoll® SD (etherified melamine formaldehyde resins), Luwipal® types such as but not limited to Luwipal® 063, Luwipal® 069 (etherified melamine formaldehyde resins), or Plastopal® types such as but not limited to Plastopal® BTM, Plastopal® BTW (etherified urea formaldehyde resins).

In suitable urea-formaldehyde or thiourea-formaldehyde pre-condensates, the molar ratios of urea or thiourea to formaldehyde are generally in the range of 1:0.8 to 1:4, in particular in the range of 1:1.5 to 1:4, especially in the range of 1:2 to 1:3.5.

In suitable melamine-formaldehyde or melamine-(thio) urea-formaldehyde pre-condensates, the molar ratios of melamine to formaldehyde are generally in the range of 1:1.5 to 1:10, in particular in the range of 1:3 to 1:8 preferably in the range of 1:4 to 1:6.

In suitable melamine-formaldehyde or melamine-(thio) urea-formaldehyde pre-condensates, the molar ratios of melamine+urea or thiourea to formaldehyde are generally in the range of 1:0.8 to 1:9, in particular from 1:2 to 1:8 preferably in the range of 1:3 to 1:6. The molar ratio of urea or thiourea to melamine is usually in the range of 5:1 to 1:50 and in particular in the range of 30:1 to 1:30.

The pre-condensates may be used in the form of etherified pre-condensates of amino compound and aldehyde. In these etherified pre-condensates the methylol groups formed by the reaction of the amino groups with formaldehyde with an alkanol or an alkandiol, in particular with a $C_1$-$C_4$-alkanol, such as methanol, ethanol, n-propanol or n-butanol, in particular methanol, or a $C_2$-$C_4$-alkandiol, such as ethylene glycol. The degree of etherification of these resins can be adjusted by the molar ratio of amino groups to alkanol which is typically in the range of 10:1 to 1:10, preferably in the range of 2:1 to 1:5.

The pre-condensates are especially selected from the group consisting of melamine-formaldehyde pre-condensates, including wholly or partially etherified melamine-formaldehyde pre-condensates, and urea-formaldehyde pre-condensates and mixtures thereof. Especially, the pre-condensate is a wholly or partially etherified melamine-formaldehyde condensate, which may contain small amounts, e.g. 1 to 20 mol.-%, based on melamine, of urea.

According to the invention, step ii. is performed in the presence of a protective colloid. Usually, at least 20%, in particular at least 50%, especially at least 70% or at least 90% or the total amount of the protective colloid present in step iii. will also be present during step ii.

The protective colloid present during step ii. may be added to the aqueous slurry of the material M provided in step i. or it may be added during step ii. Frequently, the major amount of protective present during step ii. is added to the slurry before starting the comminution of step ii. In particular at least 20%, in particular at least 50%, especially at least 70% or at least 90% of the total amount of protective colloid present during step ii. will be added to the slurry of the material M before starting the comminution of step ii.

Protective colloids suitable for the process of the invention are principally any water-soluble polymers which are known to stabilize suspensions of water-insoluble material. Suitable protective colloids may be anionic, non-ionic or cationic.

Anionic protective colloids are water-soluble polymers, which contain a plurality of anionic groups, such as carboxylate groups, sulfonate groups, phosphonate groups, sulfate groups and/or phosphate groups. The anionic groups in these anionic polymers may be partially or fully neutralized. Suitable counter ions are alkalimetal ions, such as sodium, potassium, earth alkaline ions such as magnesium or calcium, and ammonium. In case of anionic polymeric surfactants having a sulfonate group, the anionic groups are preferably at least partly neutralized.

Suitable anionic protective colloids are e.g.
anionically modified, water-soluble polysaccharides such as carboxymethylcellulose,
lignin based sulfonic acids, such as lignosulfonic acid, ethoxylated lignosulfonic acid or oxidized lignins,
arylsulfonic acid formaldehyde condensates and arylsulfonic acid formaldehyde urea condensates, such as naphthalene sulfonic acid formaldehyde condensates, phenol sulfonic acid formaldehyde condensates, cresol sulfonic acid formaldehyde condensates etc.,
homo- and copolymers of ethylenically unsaturated monomers which frequently comprise at least 20% by weight, based on the total amount of the monomers, of at least one ethylenically unsaturated monomer which comprises at least one carboxy group, sulfonic acid group, and/or phosphonic acid group incorporated within the polymer, and salts of these, in particular the alkali metal salts and ammonium salts. When the abovementioned anionic water-soluble polymers are in an aqueous medium, the sulfonic acid groups or phosphonic acid groups bonded to the main polymer chain are generally in the salt form, i.e. in the form of sulfonate groups, the phosphonic acid groups correspondingly being in the form of phosphonate groups. The counterions are then typically alkali metal ions and alkaline earth metal ions, examples being sodium ions, and calcium ions, and ammonium ions ($NH_4^+$);

Non-ionic protective colloids are water-soluble polymers, which contain a plurality non-ionic polar moieties such as carbamoyl groups, i.e. $C(=O)NH_2$ groups, lactam groups, such as pyrrolidin-2-on groups, polyethyleneoxide groups or hydroxyl groups.

Suitable non-ionic protective colloids are e.g. water-soluble starches, starch derivatives, and cellulose derivatives, such as methylcellulose, hydroxypropylcellulose, hydroxyethylcellulose, hydroxypropylmethylcellulose, and also polyvinyl alcohols, inclusive of partially hydrolyzed polyvinyl acetate with a degree of hydrolysis which is preferably at least 40%, in particular at least 60%, polyacrylamide, polyvinylpyrrolidone, polyethylene glycols, graft polymers of vinyl acetate and/or vinyl propionate onto polyethylene glycols, and polyethylene glycols mono- or bilaterally end-group-capped with alkyl, carboxy, or amino groups.

Preferably, the protective colloids are selected from anionic polymers having a plurality of sulfate or sulfonate groups, and neutral polymers having a plurality of hydroxyl groups, such as polyvinyl alcohols, inclusive of partially hydrolyzed polyvinyl acetate with a degree of hydrolysis which is preferably at least 40%, in particular at least 60%.

In a preferred embodiment of the invention, the microparticle composition contains at least one anionic protective colloid, hereinafter also referred to as anionic polymeric surfactant A, which contains a plurality of anionic groups, especially sulfonate groups or sulfate groups.

Examples for polymeric surfactant A are the surfactants of the following groups A1 to A3, including the salts thereof:
A.1 lignin based sulfonic acids, such as lignosulfonic acid, ethoxylated lignosulfonic acid or oxidized lignins;
A.2 arylsulfonic acid formaldehyde condensates and arylsulfonic acid formaldehyde urea condensates, such as naphthalene sulfonic acid formaldehyde condensates, phenol sulfonic acid formaldehyde condensates, cresol sulfonic acid formaldehyde condensates etc.;
A.3 and homo- or copolymers of monoethylenically unsaturated monomers M1 having a sulfonic acid group optionally with one or more comonomers M2 different from monomers M1.

The anionic groups in these anionic polymeric surfactants A may be partially or fully neutralized. Suitable counter ions are alkalimetal ions, such as sodium, potassium, earth alkaline ions such as magnesium or calcium, and ammonium. In case of anionic polymeric surfactants having a sulfonate group, the anionic groups are preferably at least partly neutralized.

The anionic polymeric surfactants A are in particular selected from groups A2. and A.3, especially from group A.3.

Preferably, the anionic polymeric surfactant A.3 is selected from homo- or copolymers made of
i) at least one monoethylenically unsaturated monomer M1 having a sulfonic acid group, such as vinylsulfonic acid, allylsulfonic acid, styrene sulfonic acid, vinyltoluene sulfonic acid, (meth)acrylate monomers having a sulfonic acid group, such as 2-acryloxyethylsulfonic acid, 2-acryloxypropylsulfonic or 4-acryloxybutylsulfonic acid, and (meth)acrylamide monomer having a sulfonic acid group, such as 2-acrylamidoethylsulfonic acid, 2-acrylamidopropylsulfonic acid or 2-acrylamido-2-methylpropane sulfonic acid
ii) optionally with one or more monoethylenically unsaturated comonomers M2 different from monomers M1, such as styrene, $C_1$-$C_4$-alkylacrylates, $C_1$-$C_4$-alkylmethacrylates, acrylamide, methacrylamide, acrylic acid, methacrylic acid, $C_1$-$C_4$-alkylacrylates, $C_1$-$C_4$-alkylmethacrylates.

In particular, groups of embodiments, the anionic polymeric surfactant A comprises or is selected from homo- or copolymers of group A.3, in particular from homo- or copolymers made of
i) monomers M1, which are selected from (meth)acrylate monomers having a sulfonic acid group, such as 2-acryloxyethylsulfonic acid, 2-acryloxypropylsulfonic or 4-acryloxybutylsulfonic acid, and (meth)acrylamide monomer having a sulfonic acid group, such as 2-acrylamidoethylsulfonic acid, 2-acrylamidopropylsulfonic acid or 2-acrylamido-2-methylpropane sulfonic acid,
ii) optionally with one or more monoethylenically unsaturated comonomers M2 different from monomers M1, such as styrene, $C_1$-$C_4$-alkylacrylates, $C_1$-$C_4$-alkylmethacrylates, acrylamide, methacrylamide, acrylic acid, methacrylic acid, $C_1$-$C_4$-alkylacrylates, $C_1$-$C_4$-alkylmethacrylates.

Especially, the polymeric surfactant A.3 comprises or is selected from homo- or copolymers of
i) monomers M1, which is 2-acrylamido-2-methylpropane sulfonic acid,
ii) optionally with one or more monoethylenically unsaturated comonomers M2 different from monomers M1, such as styrene, $C_1$-$C_4$-alkylacrylates, $C_1$-$C_4$-alkylmethacrylates, acrylamide, methacrylamide, acrylic acid, methacrylic acid, $C_1$-$C_4$-alkylacrylates, $C_1$-$C_4$-alkylmethacrylates.

In these preferred, particular preferred or especially preferred anionic polymeric surfactants A.3, the amount of monomers M1 is preferably at least 50% by weight, based on the total amount of monomers forming the polymeric surfactant. Even more preferred are polymeric surfactants A, which are homo- or copolymers of monomers M1, wherein the amount of monomers M1 is at least 90% by weight, based on the total amount of monomers forming the polymeric surfactant. These polymers are known and frequently commercially available e.g. from BASF SE.

In another particular groups of embodiments, the anionic polymeric surfactant A comprises or is selected from surfactants of group A.2, i.e. arylsulfonic acid formaldehyde condensates and arylsulfonic acid formaldehyde urea condensates, in particular from naphthalene sulfonic acid formaldehyde condensates.

Instead to the anionic polymeric surfactant A or in combination therewith a non-ionic protective colloid can be used. Then, the non-ionic protective colloid is preferably selected from the group consisting of neutral polymers having a plurality of hydroxyl groups, such as polyvinyl alcohols, inclusive of partially hydrolyzed polyvinyl acetate with a degree of hydrolysis which is preferably at least 40%, in particular at least 60%. The amount of the protective colloid in the composition subjected to step ii. is preferably in the range of 0.1 to 50% by weight, in particular in the range of 2 to 40% by weight and most preferred in the range of 3 to 30% by weight, based on the total amount of material M to be encapsulated and aminoplast pre-condensate.

It was found beneficial, if the protective colloid is combined with one or more further anionic emulsifiers B different from the protective colloids. The anionic emulsifiers B provide for the stabilization of an aqueous formulation comprising the microparticles. Suitable anionic emulsifiers B are surfactants having one anionic group, which is selected from phosphate or phosphonate groups and sulfate or sulfonate groups, the latter compounds being preferred. In contrast to the protective colloids, the molecular weight (number average) of these surfactants is generally lower and in particular at most 500 Dalton.

These anionic emulsifiers B will usually be included into the microparticle composition in the form of their salts, in particular the sodium, potassium or ammonium salts. Examples of anionic emulsifiers B include the salts of alkylsulfonates, alkylsulfates, alkylphosphates, semi-esters of alkoxylated alkanols with sulfuric acid or phosphoric acid, alkylarylsulfonates, alkylarylphosphates, semi-esters of alkoxylated alkylphenols with sulfuric acid or phosphoric acid and semi-esters of alkoxylated mono-, di- or tristyrylphenols with sulfuric acid or phosphoric acid. Amongst these anionic surfactants B, those of the formula I are preferred:

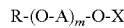

$$R\text{-}(O\text{-}A)_m\text{-}O\text{-}X \qquad I$$

wherein
R is a hydrocarbon radical having from 8 to 40 carbon atoms and preferably from 12 to 30 carbon atoms and optionally one oxygen atom;
A is independently from one another 1,2-ethylene, 1,2-propylene or 1,3-propylene, especially 1,2-ethylene;
m is from 0 to 50, preferably from 0 to 30 and especially preferred from 0 to 20; and
X is $SO_3M$ or $PO_3M_2$ with M being selected from H, alkaline metal ions, such as K and Na, alkaline earth metal ions, such as ½ Ca and ½ Mg and ammonium. Preferably, M is an alkaline metal ion and especially sodium.
Examples of suitable hydrocarbon radicals R having from 8 to 40 carbon atoms are alkyl having from 8 to 40 and preferably from 12 to 30 carbon atoms, phenyl, which may be substituted with one or two alkyl radicals having from 4 to 20 carbon atoms, phenyl, which is substituted with a phenoxy radical, wherein phenyl and/or phenoxy may contain an alkyl radical having from 4 to 20 carbon atoms, tristyrylphenyl radical etc. In a preferred embodiment of the present invention the radical R in formula I is a tristyrylphenyl radical.

Preference is given to anionic emulsifiers B, which are of the formula (I), wherein R, m and X have the following meanings:
R is alkyl having from 8 to 30, in particular from 10 to 20 carbon atoms,
m is 0,
X is $SO_3M$ with m being selected from alkaline metal ions, such as K and Na, alkaline earth metal ions, such as ½ Ca and ½ Mg and ammonium. Preferably, M is an alkaline metal and especially sodium.

If present, the amount of anionic emulsifiers B, in particular the surface-active compound of the formula I, is preferably in the range of 0.1 to 10% by weight, in particular from 0.3 to 7% by weight and most preferred in the range of 0.5 to 5% by weight, based on the total amount of material M and aminoplast pre-condensate. If present, the amount of anionic emulsifier B, in particular the surface-active compound of the formula I, is preferably chosen such that the weight ratio of protective colloid to anionic emulsifier B is in the range of 1:1 to 20:1 in particular in the range of 2:1 to 10:1.

In step ii. of the process of the invention, the coarse particles of the material M are comminuted to the particle size required in the encapsulation step iii. Usually, comminution is performed such that less than 10% by weight of the particles of the material M have a particle diameter of 40 µm or larger, i.e. the d(0.9) value is at most 40 µm, in particular at most 30 µm and especially at most 25 µm. Preferably, comminution is performed such that the volume average particle diameter d(0.5) of the material M is at most 25 µm or lower, e.g. in the range of 0.5 to 25 µm, in particular in the range of 0.5 to 15 µm and especially in the range of 0.5 to 10 µm.

Step ii. may be carried out by any physical comminution method suitable for achieving comminution of solid particles in an aqueous suspension, including grinding or milling techniques, respecitvly, i.e. wet grinding or wet milling, but also application of ultrasound or high pressure homogenization. In the instant application, the terms "grinding" and "milling" are synonymic. Preferably, comminution is achieved by applying mechanical comminution methods, i.e. by subjecting the suspension to strong shear forces by mechanical means in a suitable comminution device. Suitable mechanical comminution methods are in particular wet grinding or wet milling techniques, such as wet grinding or wet milling in a milling device such as tumbling mills, including ball mills and rod mills, stirred media mills, including agitator bead mills, rotor-stator mills and the like. Suitable mechanical wet grinding/milling methods and grinding devices are known, e.g. from Perry's Chemical Engineers' Handbook, 7th ed. McGraw Hill 1997, 20-31 to 20-38, and commercially available, e.g. from Netzsch Feinmahltechnik, FHZ GmbH, Hosokawa-Alpine AG, Willy A. Bachofen AG Maschinenfabrik and Buhler GmbH.

In particular embodiments of the invention, step ii. is carried out in a stirred media mill, also termed agitated media mill. In other words, step ii. is performed by agitating the suspension together with a media of hard particles, which are harder than the particles of the material M, such that the particles of the material M and the hard particles collide, and the particles are broken in these collisions. The media of hard particles is also referred to as grinding media.

In the stirred media mill, the grinding media is stirred in a closed or open milling chamber, preferably closed milling chamber. The preferred method of stirring is by means of a stirrer comprising a rotating shaft. The shaft may be provided with disks, arms, pins, or other grinding devices. The stirred media mill may be operated in a batch or continuous mode. The stirred media mill may be operated in a vertical or horizontal position, the latter being preferred.

Preferably, the stirred media mill is operated in a continuous mode in which the suspension is recirculated to the inlet of the mill. Recirculation of the product can be driven by conventional means, such as by employing a peristaltic pump. Preferably, the product is recirculated as quickly as possible to achieve a high number of turnovers. The required residence time for achieving the desired fineness will depend on several factors, such as the energy impact, the hardness of the material, the design of the milling apparatus and other features of the milling process, mentioned above. However, a skilled person will be readily in the position to evaluate the required residence time by routine experiments.

Suitable grinding media for the practice of the present invention include metal beads and ceramic beads. Suitable metal beads include beads of carbon steel and beads of stainless steel. Preferred ceramic beads include beads of zirconium oxide, beads of yttrium or cerium stabilized zirconium oxide, beads of zirconium silicate, and beads of alumina. The preferred grinding media for the purpose of the invention are beads of yttrium stabilized zirconium oxide.

The grinding media used for particle size reduction are preferably spherical. The grinding media for the practice of the present invention preferably have an average size ranging from about 50 to 2000 microns (0.05 to 2.0 mm), more preferably from about 200 to 1000 microns (0.2 to 1.0 mm).

Preferably the grinding media load measured as a volume percent of the mill chamber volume is 60 to 90%, more preferably 70 to 85%.

Stirred media mills are operated at tip speeds in the range of 3 to 15 m/s. Preferably in the range of 8 to 12 m/s.

Suitable agitated media mills are commercially available, e.g. from Netzsch Feinmahltechnik, Willy A. Bachofen AG Maschinenfabrik and Bühler GmbH.

Step ii. may be performed by using a single comminution device. However, it is also possible to combine two or more comminution devices in series.

According to the invention, step ii. is performed in the presence of a protective colloid. The amount of the protective colloid in the composition subjected to step ii. is frequently from 0.1 to 50% by weight, in particular from 2 to 40% by weight and most preferred from 3 to 30% by weight, based on the total amount of material M to be encapsulated and aminoplast pre-condensate. The concentration of the protective colloid in the suspension subjected to step ii. is usually in the range of 0.1 to 10%, in particular from 0.2 to 8% and especially from 0.3 to 5%, based on the total weight of the suspension subjected to step i.

According to the invention, step ii. is performed in the presence of an aminoplast pre-condensate. During step ii. the concentration of the aminoplast pre-condensate in the suspension subjected to step ii. is frequently in the range of 0.5 to 30% by weight, in particular from 1 to 10% by weight, based on the total weight of the suspension.

The concentration of the material M in the suspension subjected to step ii. is frequently in the range of 5 to 40% by weight, in particular in the range of 7 to 35% by weight, based on the total weight of the suspension.

If present, the concentration of the surfactant B in the suspension subjected to step ii. is frequently in the range of 0.001% by weight to 2% by weight, in particular from 0.01 to 1% by weight, based on the total of the suspension.

Preferably, step ii. is performed at a temperature, which is below the melting point of the material M, in particular at a temperature which is at least 10° C., in particular at least 20° C. below the melting point of the material M.

The polycondensation of the aminoplast pre-condensate can be effected or initiated in a well-known manner, e.g. by heating the aqueous suspension obtained in step ii. to a certain reaction temperature, at a pH, where the polycondensation at the reaction temperature occurs. During the polycondensation, the aminoplast pre-condensate is converted into a water-insoluble aminoplast resin, which precipitates from the aqueous phase and deposits preferably on the surface of the solid particles material M, thereby embedding or surrounding the material M.

Preferably, the polycondensation of the aminoplast is performed at pH of less than pH 6, in particular at a pH of at most pH 5, especially at a pH of at most pH 4, e.g. in the range of pH 0 to 6, more particularly in the range from pH 1 to 5 or in the range from pH 2 to 4.

The pH of the aqueous suspension is usually adjusted by addition of suitable amounts of an organic or inorganic acid, such as sulfuric acid, hydrochloric acid, phosphoric acid, a carboxylic acid including alkanoic acids, alkandioic acids or hydroxycarboxylic acids, such as formic acid, acetic acid, propionic acid, oxalic acid, malic acid or citric acid, and alkyl or arylsulfonic acids, such as methanesulfonic acid or toluenesulfonic acid. It is preferred, but not mandatory, if at least a portion, in particular the majority of the acid is present in the aqueous suspension, before the aqueous suspension is heated to the reaction temperature.

Preferably, the polycondensation of the aminoplast pre-condensate is performed at elevated temperature, in particular at a temperature of at least 40° C., in particular at least 50° C., e.g. at a temperature in the range of 40 to 100° C., in particular in the range of 45 to 95° C. or in the range of 50 to 90° C. It may be possible to effect the start of the polycondensation of the aminoplast at a comparatively low temperature, e.g. a temperature in the range of 40 to 65° C. or 45 to 60° C. and then complete the polycondensation reaction at a higher temperature of e.g. 50 to 100° C. or 60 to 90° C. The time for completing the polycondensation may vary, depending on the reactivity of the pre-condensate, the temperature and the pH of the aqueous suspension and may take from 1 h to 24 h, in particular from 2 to 12 h. Preferably, the polycondensation reaction is at least partly performed at temperatures of at least 50° C., in particular at least 60° C., e.g. for 1 to 8 h at a temperature in the range from 50 to 100° C., in particular 60 to 90° C.

It is possible to perform steps ii. and iii. successively. It is, however also possible to combine steps ii. and iii., i.e. to perform polycondensation while still performing step ii.

If steps ii. and iii. are performed successively, one will perform step ii. first, until the desired particle size of the material M is achieved, and then perform step iii. by effecting the polycondensation of the aminoplast pre-condensate as described above. Then, steps ii. and iii. are frequently performed in separate vessels, i.e. step ii. is performed in a suitable device for comminution of the particles of the material M, such as an agitated media mill, and then the obtained suspension of the material M is transferred into a reaction vessel, where the polycondensation is effected as described above.

If steps ii. and iii. are combined in a single step, polycondensation of step iii. is performed while still performing comminution step ii. It is not necessary to start polycondensation together with comminution. Rather, one will preferably start with step ii. and continue step ii. while starting the polycondensation of step iii. In particular, the slurry of step i. is subjected to step ii. until a certain fineness of the particles in the suspension is achieved and then polycondensation is started by lowering pH and/or by increasing the temperature, while still further performing means for comminuting the particles. For example, the slurry of step i. is transferred to a milling device, e.g. an agitated media mill and subjected to comminution, until the d(0.9) value is below 40 µm, in particular below 30 µm or below 20 µm, and then, the suspension is heated, e.g. to a temperature of at least 50° C. or at least 60° C. and the pH of the suspension is lowered, e.g. to a pH of at most 5.0, in particular at most 4.0 while further subjecting the suspension to comminution in the milling device, e.g. agitated media mill. It is also possible, for example, to transfer the slurry of step i. to a milling device, e.g. an agitated media mill and subjected to comminution, until the d(0.9) value is below 40 µm, in particular below 30 µm or below 20 µm, discharging the suspension from the milling device, followed by effecting the conditions for polycondensation, e.g. by heating the suspension, e.g. to a temperature of at least 50° C. or at least 60° C., and lowering the pH of the suspension, e.g. to a pH of at most 5.0, in particular at most 4.0, and then recharging the suspension to the milling device and subjecting the suspension to comminution in the milling device.

The microcapsules/microparticles obtained by the process of the present invention are discrete particles having usually a particle size of less than 200 µm, frequently less than 100 µm and in particular less than 50 µm, given as d(0.9) value. Preferably, the particle size of the microcapsule particles, i.e. their diameter, will not exceed 40 µm, in particular not exceed 35 µm and especially not exceed 30 µm. The particle size given is the so called d(0.9)-value as defined above. The microcapsule particles frequently have an average particle diameter, herein also termed d(0.5)-value, ranging from 0.5 to 25 µm, in particular from 0.5 to 20 µm, especially from 0.5 to 10 µm.

The concentration of the material M in the suspension obtained in step iii. is frequently in the range of 3 to 40% by weight, in particular in the range of 5 to 35% by weight, based on the total weight of the suspension.

The thus obtained aqueous dispersion of the microparticles or microcapsules, respectively, may be neutralized by the addition of a base. Preferably, the pH of the dispersion is adjusted to a pH of at least 6, e.g. a pH in the range of pH 6 to 10, in particular in the range of pH 6.5 to 9.0.

From the aqueous suspension obtained by the process as described herein, the microparticles can be isolated, e.g. by filtration or centrifugation, or the aqueous suspension may be spray-dried, granulated or freeze-dried, to obtain a solid composition in the form of a powder or granules. The solid composition may be re-dispersed or formulated by using formulation auxiliaries as described below.

Customary formulation auxiliaries include, e.g. viscosity-modifying additives (thickeners), antifoam agents, preservatives, buffers, inorganic dispersants, etc., which are usually employed in aqueous formulations. Such auxiliaries may be incorporated into the aqueous suspension, after step iii) of the preparation process described herein has been carried out. The amount of additives will generally not exceed 10% by weight, in particular 5% by weight of the total weight of the aqueous suspension.

Suitable inorganic dispersants, also termed anticaking agents, for preventing agglutination of the microparticles, are silica (such as, for example Sipernat® 22 from Degussa), alumina, calcium carbonate and the like. In the context of the present invention silica is a preferred inorganic dispersant. The concentration of inorganic dispersants in the final suspension will generally not exceed 2% by weight, based on the total weight of the final suspension, and, if present, it is preferably in the range from 0.01 to 2% by weight, in particular from 0.02 to 1.5% by weight and especially from 0.1 to 1% by weight, based on the total weight of the final formulation.

Suitable thickeners are compounds which affect the flow behavior of the suspension concentrate and may assist in stabilizing the aqueous suspension of the microparticles against caking. Mention may be made, in this connection, for example, of commercial thickeners based on polysaccharides, such as methylcellulose, carboxymethylcellulose, hydroxypropylcellulose (Klucel® grades), Xanthan Gum (commercially available e.g. as Kelzan® grades from Kelco or Rhodopol® grades from Rhodia), synthetic polymers, such as acrylic acid polymers (Carbopol® grades), polyvinyl alcohol (e.g. Mowiol® and Poval® grades from Kuraray) or polyvinyl pyrrolones, silicic acid or phyllosilicates, such as montmorillonite and bentonites, which may be hydrophobized, (commercially available as Attaclay® grades and Attaflow® grades from BASF SE; or as Veegum® grades and Van Gel® grades from R.T. Vanderbilt). The concentration of thickeners in the aqueous suspension will generally not exceed 2% by weight, based on the total weight of the aqueous suspension, and is preferably in the range from 0.01 to 2% by weight, in particular from 0.02 to 1.5% by weight and especially from 0.1 to 1% by weight, based on the total weight of the aqueous suspension or the final formulation, respectively.

Antifoam agents suitable for the compositions according to the invention are, for example, silicone emulsions (such as, for example, Silicone SRE-PFL from Wacker or Rhodorsil® from Bluestar Silicones), polysiloxanes and modified polysiloxanes including polysiloxane blockpolymers such as FoamStar® SI and FoamStar® ST products of BASF SE, long-chain alcohols, fatty acids, organofluorine compounds and mixtures thereof.

Suitable preservatives to prevent microbial spoiling of the compositions of the invention include formaldehyde, alkyl esters of p-hydroxybenzoic acid, sodium benzoate, 2-bromo-2-nitropropane-1,3-diol, o-phenylphenol, thiazolinones, such as benzisothiazolinone, 5-chloro-2-methyl-4-isothiazolinone, pentachlorophenol, 2,4-dichlorobenzyl alcohol and mixtures thereof. Commercially available preservatives that are based on isothiazolinones are for example marketed under the trademarks Proxel® (Arch Chemical), Acticide® MBS (Thor Chemie) and Kathon® MK (Rohm & Haas).

If appropriate, the compositions according to the invention, in particular the aqueous suspensions, may comprise buffers to regulate the pH. Examples of buffers are alkali metal salts of weak inorganic or organic acids such as, for example, phosphoric acid, boric acid, acetic acid, propionic acid, citric acid, fumaric acid, tartaric acid, oxalic acid and succinic acid.

In addition, the compositions according to the invention, in particular the aqueous suspensions, can be formulated with conventional binders, for example aqueous polymer dispersions, water-soluble resins, for example water-soluble alkyd resins, or waxes.

The aqueous dispersions of microcapsules obtainable by the process as defined herein contain an agriculturally active compound. Consequently, they can be used for controlling harmful organisms, such phytopathogenic fungi, undesired plants, undesired insect or mite, and/or for regulating the growth of plants, depending on the type of agriculturally active compound. Hence, the invention also relates to the use of an aqueous dispersion of microcapsules obtainable by a process as defined herein for controlling phytopathogenic fungi and/or undesired plant growth and/or undesired insect or mite attack and/or for regulating the growth of plants.

The aqueous dispersions can be applied as such or in formulated form in a customary manner. Therefore, the invention also relates to a method of controlling phytopathogenic pests, in particular for controlling phytopathogenic fungi and/or undesired plant growth and/or undesired insect or mite attack, wherein the aqueous dispersion of microcapsules obtainable by a process as defined herein is allowed to act on the respective pests, their environment or the crop plants to be protected from the respective pest, on the soil and/or on undesired plants and/or on the crop plants and/or on their environment. The invention also relates to a method for regulating the growth of plants, wherein the aqueous dispersion of microcapsules obtainable by a process as defined herein is allowed to act on the crop plants the crop plants and/or on their environment.

When employed in plant protection, the amounts of active compound applied are, depending on the kind of desired effect, from 0.001 to 2 kg per ha, preferably from 0.005 to 2 kg per ha, more preferably from 0.05 to 0.9 kg per ha, in particular from 0.1 to 0.75 kg per ha. In treatment of plant propagation materials such as seeds, e. g. by dusting, coating or drenching seed, amounts of active compound of from 0.1 to 1000 g, preferably from 1 to 1000 g, more preferably from 1 to 100 g and most preferably from 5 to 100 g, per 100 kilogram of plant propagation material (preferably seed) are generally applied. When used in the protection of materials or stored products, the amount of active compound applied depends on the kind of application area and on the desired effect. Amounts customarily applied in the protection of materials are 0.001 g to 2 kg, preferably 0.005 g to 1 kg, of active compound per cubic meter of treated material.

Depending on the type of active compound, the dispersion of the microcapsules or a formulation thereof may be used for the purposes of treatment of plant propagation materials, particularly seeds. The dispersions in question give, after two-to-tenfold dilution, active compound concentrations of from 0.01 to 20% by weight, preferably from 0.1 to 15% by weight, in the ready-to-use preparations. Application can be carried out before or during sowing. Methods for applying the dispersion on to plant propagation material or treating the plant propagation material therewith, especially seeds, include dressing, coating, pelleting, dusting, soaking and in-furrow application methods of the propagation material. Preferably, the respective dispersion or a formulation thereof, is applied on to the plant propagation material by a method such that germination is not induced, e. g. by seed dressing, pelleting, coating and dusting.

Various types of oils, wetters, adjuvants, fertilizer, or micronutrients, and other pesticides (e.g. herbicides, insecticides, fungicides, growth regulators, safeners) may be added to the respective dispersion or a formulations thereof as premix or, if appropriate not until immediately prior to use (tank mix). These agents can be admixed with the compositions according to the invention in a weight ratio of 1:100 to 100:1, preferably 1:10 to 10:1.

The user applies the respective dispersion or a formulation thereof usually from a predosage device, a knapsack sprayer, a spray tank, a spray plane, or an irrigation system. Usually, the respective dispersion or a formulation thereof is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

Examples of suitable crop plants are cereals, for example wheat, rye, barley, triticale, oats or rice; beet, for example sugar or fodder beet; pome fruit, stone fruit and soft fruit, for example apples, pears, plums, peaches, almonds, cherries, strawberries, raspberries, currants or gooseberries; legumes, for example beans, lentils, peas, lucerne or soybeans; oil crops, for example oilseed rape, mustard, olives, sunflowers, coconut, cacao, castor beans, oil palm, peanuts or soybeans; cucurbits, for example pumpkins/squash, cucumbers or melons; fiber crops, for example cotton, flax, hemp or jute; citrus fruit, for example oranges, lemons, grapefruit or tangerines; vegetable plants, for example spinach, lettuce, asparagus, cabbages, carrots, onions, tomatoes, potatoes, pumpkin/squash or capsicums; plants of the laurel family, for example avocados, cinnamon or camphor; energy crops and industrial feedstock crops, for example maize, soybeans, wheat, oilseed rape, sugar cane or oil palm; maize; tobacco; nuts; coffee; tea; bananas; wine (dessert grapes and grapes for vinification); hops; grass, for example turf; sweetleaf (Stevia rebaudania); rubber plants and forest plants, for example flowers, shrubs, deciduous trees and coniferous trees, and propagation material, for example seeds, and harvested produce of these plants.

The term crop plants also includes those plants which have been modified by breeding, mutagenesis or recombinant methods, including the biotechnological agricultural products which are on the market or in the process of being developed. Genetically modified plants are plants whose genetic material has been modified in a manner which does not occur under natural conditions by hybridizing, mutations or natural recombination (i.e. recombination of the genetic material). Here, one or more genes will, as a rule, be integrated into the genetic material of the plant in order to improve the plant's properties. Such recombinant modifications also comprise posttranslational modifications of proteins, oligo- or polypeptides, for example by means of glycosylation or binding polymers such as, for example, prenylated, acetylated or farnesylated residues or PEG residues.

I. Analytics

Particle size Distribution (PSD) was determined by statistic laser scattering using a Malvern Mastersizer 200 according to European norm ISO 13320 EN. The data were treated according to the Mie-Theory by software using a "universal model" provided by Malvern Instruments. Important parameters are the $d_n$-values for n=10, 50 and 90, the $d_{10}$, $d_{50}$ and $d_{90}$.

Solid content of the final dispersion was measured by evaporating the volatiles of small probe of the aqueous suspension in an oven at 105° C. for 2 hours. The value indicated for the examples is an average value from three parallel experiments.

II. Ingredients

Protective colloid 1: 20% aqueous solution of poly(2-acrylamido-2-methylpropane sulfonic acid) sodium salt with pH 2.5-4;
Protective colloid 2: Naphthalenesulfonic acid formaldehyde condensate Sodium salt Surfactant 1: 15% aqueous solution of sodium dodecyl sulfate Pre-condensate P1: 70% w/w aqueous solution of etherified melamine formaldehyde pre-condensate (Luracoll® SD of BASF SE);

Thickener: Viscalex HV 30® (30% aqueous solution of an acrylic polymer; BASF SE)

Saflufenacil: Anyhdrate, purity 98.8%

Pyrimethanil: Crystalline, purity>98%

For the following experiments a MicroCer® bead mill of Netzsch Feinmahltechnik GmbH, Germany having an internal volume of 80 mL and a ZETA® agitator of Netzsch Feinmahltechnik GmbH was used. A sieve (200 μm) was installed inside the mill at the outlet. The mill was connected with a vessel and operated in a circuit mode.

EXAMPLE 1

The stirred media mill was filled with zircon oxide grinding media with an average diameter of 0.6-0.8 mm. Filling degree was 62.5% of the internal volume.

150 g crystalline saflufenacil anhydrate was mixed with 790.4 g water, 20 g protective colloid 2, 2.7 g surfactant 1 and 36.9 g aminoplast pre-condensate P1 in a stirred vessel until a homogenous suspension was obtained.

The above slurry was subjected to milling. The mill was operated at a tip speed that averaged 12 m/s. The suspension was passed through the mill by circuit mode. After 2 hours of grinding the average particle size, by volume d(0.5), was reduced to 1.6 μm and 90% of the particles had sizes of less than 4.0 μm.

The thus obtained suspension was stable for several hours and could be processed in the following encapsulation step.

The suspension was transferred into a reaction vessel equipped with a stirrer. Then the suspension was warmed to 30° C. and 41 g of a 10% aqueous formic acid with stirring. Stirring was continued for further 1 h at 30° C. at 250 rpm. Then, the reaction vessel was slowly heated within 60 min to 80° C. and the temperature was kept at 80° C. for further 120 min with stirring. Then the reaction vessel was cooled to 22° C.

The obtained aqueous suspension had a content of saflufenacil of 15.0% by weight. The d(0.5) value was 1.7 μm, d(0.9) was 4.4 μm.

EXAMPLE 2

Composition: 230 g saflufenacil anhydrate, 20 g protective colloid 2, 2,7 g surfactant 1 and 36.9 g aminoplast condensate P1, 710,4 g water Apparatus settings and parameters for the mixing and milling were chosen according to Example 1. After milling particle size by volume d(0.5), was reduced to 1.6 μm and 90% of the particles had sizes less than 3.8 μm. The polymerization was performed under the conditions of Example 1.

The obtained aqueous suspension had a content of saflufenacil of 23% by weight. The d(0.5) value was 12.1 μm, and d(0.9) was 63.9 μm.

EXAMPLE 3

Composition: 300 g saflufenacil anhydrate, 20 g protective colloid 2, 2,7 g surfactant 1 and 36.9 g aminoplast pre-condensate P1, 710,4 g water Apparatus settings and parameters for the mixing and milling were chosen according to Example 1. After milling particle size by volume d(0.5), was reduced to 1.3 micron and 90% of the particles had sizes less than 3.0 μm. The polymerization was performed under the conditions of Example 1.

The obtained aqueous suspension had content of saflufenacil of 30% by weight. The d(0.5) value was 7.4 μm and d(0.9) was 190.0 μm.

EXAMPLE 4

Composition: 240 g saflufenacil anhydrate, 29 g protective colloid 2, 17 g surfactant 1, 55 g aminoplast pre-condensate P1, 659 g water.

Apparatus settings and parameters for the mixing and milling were chosen according to Example 1. The polymerization was performed under the conditions of Example 1.

The obtained aqueous suspension had content of saflufenacil of 24% by weight. The d(0.5) value was 2.4 μm and d(0.9) was 4.9 μm.

EXAMPLE 5

Composition: 160.2 g saflufenacil anhydrate, 11.9 g surfactant 1, 57.84 g protective colloid 1, 36.36 g aminoplast pre-condensate P1, 382.24 g water.

Apparatus settings and parameters for the mixing and milling were chosen according to Example 1. The polymerization was performed under the conditions of Example 1.

The obtained aqueous suspension had a content of saflufenacil of 24% by weight. The d(0.5) value was 3.1 μm.

EXAMPLE 6

Composition: 227 g Pyrimethanil, 164 g protective colloid 1, 17 g surfactant 1, 51 g aminoplast pre-condensate P1, 519 g water.

Apparatus settings and parameters for the mixing and milling were chosen according to Example 1. The polymerization was performed under the conditions of Example 1.

The obtained aqueous suspension had a content of pyrimethanil of 23% by weight. The d(0.5) value was 8.4 μm and d(0.9) was 14.0 μm.

EXAMPLE 7

Composition: 100 g Pyrimethanil, 72 g protective colloid 1, 8 g surfactant 1, 15, 23 g aminoplast pre-condensate P1, 797 g water.

The above composition was subjected to milling. Milling parameters during milling were chosen according to Example 1. After having milled the suspension for 2 hours in the presence of the aminoplast pre-condensate, the tip speed of the mill was reduced from 12 m/s to 3.6 m/s and the vessel was heated until the milled suspension had a temperature of 80° C. Once the temperature was reached, formic acid was added into the vessel during constantly stirring the suspension in the vessel and the suspension was pumped through the stirred media mill until a pH of 3.5 was achieved. Thereafter, the suspension was milled for 2 further hours at 3.6 m/s in circuit mode at a temperature of 80° C. and the pH of 3.5.

The obtained aqueous suspension had a solid content of 7% by weight. The d(0.5) value was 8.4 μm, the d(0.9) was 32.7 μm.

EXAMPLE 8

Composition: 100 g Pyrimethanil, 72 g protective colloid 1, 8 g surfactant 1, 23 g aminoplast pre-condensate P1, 797 g water.

The above composition was subjected to milling. Milling parameters were chosen according to Example 1, with the exception, that the temperature of the slurry was adjusted to 80° C. before the milling was started. Once the temperature of 80° C. was reached, the suspension was pumped through the mill by circuit mode and comminuted with 12 m/s stirrer tip speed. After the milling had been started, formic acid was added into the vessel in an amount that a pH of 3.5 was obtained. The sample was milled for further 2 hours at a tip speed of 12 m/s and a temperature of 80° C.

The obtained aqueous suspension had a solid content of 7% by weight. The d(0.5) value was 13.9 µm, the d(0.9) was 30.0 µm.

EXAMPLE 9

Composition: 66.7 g saflufenacil, 5.0 g surfactant 1, 24.1 g protective colloid 1, 15.2 g aminoplast pre-condensate P1, 539 g deionised water.

The above composition was subjected to milling. Milling parameters were chosen according to Example 1, with the exception, that the temperature of the slurry was adjusted to 80° C., before the milling was started. Once the temperature of 80° C. was reached, the suspension was pumped through the mill by circuit mode and comminuted with 12 m/s stirrer tip speed. After the milling had been started, formic acid was added into the vessel until a pH of 3.5 was obtained. The sample was milled for further 2 hours at a tip speed of 12 m/s and a temperature of 80° C.

The obtained aqueous suspension had a content of saflufenacil of 10% by weight. The d(0.5) value was 19 µm.

We claim:

1. A process for preparing an aqueous dispersion of microcapsules containing a water-insoluble solid organic material selected from agriculturally active compounds and an aminoplast resin that surrounds or embeds the water-insoluble solid organic material, the process comprising the following steps:
   i. providing an aqueous slurry of a water-insoluble solid organic material in a form of coarse particles;
   ii. subjecting the aqueous slurry to shear forces in order to comminute the coarse particles, wherein an aqueous suspension of fine particles of the water-insoluble solid organic material is obtained; and
   iii. performing a polycondensation of an aminoplast pre-condensate in the aqueous suspension obtained in step ii;
   wherein the subjecting the aqueous slurry to shear forces of step ii is performed in the presence of at least one protective colloid and at least a portion of the aminoplast pre-condensate subjected to the polycondensation of step iii;
   wherein the protective colloid is selected from the group consisting of a homo-or copolymer of a (meth) acrylate monomer having a sulfonic acid group, a (meth) acrylamide monomer having a sulfonic acid group, arylsulfonic acid formaldehyde condensates, and mixtures thereof.

2. The process of claim 1, wherein the aminoplast pre-condensate is selected from the group consisting of melamine formaldehyde pre-condensates, urea formaldehyde pre-condensates, and mixtures thereof.

3. The process of claim 2, wherein the aminoplast pre-condensate comprises an etherified melamine formaldehyde pre-condensate.

4. The process of claim 1, wherein at least 50% of the aminoplast pre-condensate subjected to the polycondensation of step iii is present in the aqueous suspension during step ii.

5. The process of claim 1, wherein the aminoplast pre-condensate is present in the aqueous suspension of step ii in an amount from 1 to 30% by weight, based on water-insoluble solid organic material to be encapsulated.

6. The process of claim 1, wherein the aqueous suspension of step ii additionally contains at least one anionic emulsifier different from the protective colloid.

7. The process of claim 1, wherein the coarse particles of the water-insoluble solid organic material are milled to a volume average particle diameter in a range from 0.5 to 25 µm, as determined by dynamic light scattering.

8. The process of claim 1, wherein the comminution in step ii is performed by grinding.

9. The process of claim 8, wherein the comminution in step ii is performed in a stirred media mill.

10. The process of claim 1, wherein a concentration of the water-insoluble solid organic material in the aqueous slurry of step i is from 5 to 40% by weight.

11. The process of claim 1, wherein the water-insoluble solid organic material is selected from organic compounds having a melting point above 50° C.

12. The process of claim 1, wherein at least 50% of the aminoplast pre-condensate subjected to the polycondensation of step iii and at least 50% of the protective colloid are contained in the aqueous suspension of the water-insoluble solid organic material prior to the comminution.

13. The process of claim 1, wherein the aqueous suspension of the water-insoluble solid organic material has a pH of at least 6 during the comminution in step ii.

14. The process of claim 1, wherein the polycondensation of the aminoplast pre-condensate in the aqueous suspension obtained in step ii is performed at a pH of at most 5.

15. The process of claim 1, wherein the aqueous suspension of the water-insoluble solid organic material has a pH in a range of 6.5 to 9.0 during the comminution in step ii, and wherein the polycondensation of the aminoplast pre-condensate in the aqueous suspension obtained in step ii is performed at a pH in a range of 2 to 4.

* * * * *